(12) United States Patent
Gen

(10) Patent No.: US 7,951,590 B2
(45) Date of Patent: May 31, 2011

(54) STORAGE AGENT FOR PRESERVATION OF AN ANIMAL CELL, TISSUE OR ORGAN, AND PRESERVED PROCESS OF THE SAME

(75) Inventor: Shokyu Gen, Kyoto (JP)

(73) Assignee: MG Pharmacy Ltd., Tokyo (JP)

(*) Notice: Subject to any disclaimer, the term of this patent is extended or adjusted under 35 U.S.C. 154(b) by 0 days.

(21) Appl. No.: 09/571,960

(22) Filed: May 15, 2000

(65) Prior Publication Data

US 2002/0164795 A1 Nov. 7, 2002

(30) Foreign Application Priority Data

Jun. 2, 1999 (JP) .................................. 11-192204

(51) Int. Cl.
*C12N 5/07* (2010.01)
*C12N 1/00* (2010.01)
*A01N 1/00* (2006.01)
*A01N 1/02* (2006.01)

(52) U.S. Cl. ........... 435/374; 435/1.1; 435/1.2; 435/1.3; 435/404

(58) Field of Classification Search .................. 435/2, 1, 435/374, 1.2
See application file for complete search history.

(56) References Cited

U.S. PATENT DOCUMENTS

| 4,268,517 A | * | 5/1981 | Niebes et al. | 424/283 |
| 5,284,588 A | * | 2/1994 | Makowski et al. | 210/683 |
| 5,681,845 A | * | 10/1997 | Janzen et al. | 514/424 |

FOREIGN PATENT DOCUMENTS

| EP | 0845264 | | 6/1998 |
| FR | 2475737 | * | 8/1981 |
| FR | 2651132 | | 3/1991 |
| JP | 2823707 | * | 11/1998 |

OTHER PUBLICATIONS

Lin et al. J. Agric. Food. Chem. 1996. vol. 44, pp. 1387-1394.*
Ruch et al. Carcinogenesis. 1989. vol. 10, No. 6, pp. 1003-1008.*
The Merck Index. 12th. edition. 1996, pp. 312,313,578,661,825,1262,1381,1375,1376,1402,1550.*
Phillips. Toxicology in Vitro. 1996, 10:69-76.*
Yang et al. "The Chemistry of Tea", Feb. 1996, pp. 1-2. (web page retrieved at http://www.teatalk.com/science/chemistry.htm).*
Liang-Hue Lu et al. British Journal of Pharmacology. 1998, 124(6):1227-1237.*
Hii et al. J. Endocr. 1985, 107:1-8.*
Polette et al. Thrombosis and Haemostasis. 1996, vol. 75, No. 6, pp. 945-949.*
Wheeler S.R. "Tea and Tannins". Science, Apr. 1979, vol. 204, pp. 6 and 8.*
Jan. 1, 1994 "The effects of various antioxidants on lipid peroxidation in stored whole blood." Joseph A. Knight. Biosciences Information Service vol. 24, No. 4 pp. 294-301.
Jun. 1, 1998 In vitro and in vivo Studies on the Radical-Scavenging Activity of Tea Yokozawa et al. Journal of Agricultural and Food Chemistry, US, American Chemical Society vol. 46, No. 6 pp. 2143-2150.
Apr. 1, 1998 "Inhibition of Endothelial Cell Mediated Low-Density Lipoprotein Oxidation by Green Tea Extracts". Pearson, D. A. et al. Journal of Agricultural and Food Chemistry. vol. 46, No. 4 pp. 1445-1449.
Sep. 1, 1998 "Protective action of plant polyphenols on radiation-induced chromatid breaks in cultured human cells." Parshad Ram et al. Biosciences Information Service. vol. 18, No. 5A pp. 3263-3266.
Dec. 1, 1998 "-Epigallocatechin-3-gallate inhibition of ultraviolet B-induced AP-1 activity." Barthelman Margaret et al. Biosciences Information Service. vol. 19, No. 12 pp. 2201-2204.
Mar. 15, 1994 06070758 Inventor: Seto Haruo Applicant: Ajinomoto Co Inc Patent Abstracts of Japan vol. 18, No. 316 Abstract.

* cited by examiner

*Primary Examiner* — Vera Afremova
(74) *Attorney, Agent, or Firm* — Jordan and Hamburg LLP

(57) ABSTRACT

The present invention relates to a storage agent for preservation of an animal cell, animal tissue or organ and a method of preserving an animal cell, animal tissue, animal blood or an organ. The storage agent has polyphenol as an effective ingredient. The storage agent stabilizes protein or is added to blood, corpuscles or platelets. Also, the storage agent prevents or treats an organ injury caused by a transplant operation.

13 Claims, No Drawings

STORAGE AGENT FOR PRESERVATION OF AN ANIMAL CELL, TISSUE OR ORGAN, AND PRESERVED PROCESS OF THE SAME

BACKGROUND OF THE INVENTION

1. Field of the Invention

The present invention relates to the storage agent for preservation of an animal cell or organ and preserved process, particularly the storage agent applied for animal cells, transplant internal organs, blood, corpuscle or blood platelet, stabilizer of protein and the storage agent prevented, treated and improved organ injury caused on an organ transplant operation.

2. Description of the Related Art

Ordinary method of cell storage is employed preserving method by freezing at extra low temperature of $-196°$ C. and original cell is gotten by rapid thawing of frozen cell as needs arises. However, the survival ratios of cells after thawing and fusion is low, depending on a kind of cells and examiner's skill, while those of normal and useful cells such as Langerhans islets and liver cells except cancer cell is about 10 to 30%.

Moreover, in case of bloods, corpuscle or blood platelet, the period of validity is a very short time of 12 to 72 hours because of impossibly preserving by freezing. Inspite of a fact that transplanting an internal organ recently increases, preserving method for transplanted organ still confront researcher as serious theme. These problems are greatly related to cell damage and tissue injury.

As a result of a progress in surgical operation and immunosuppressive agent, case of transplanting an internal organ recently increases. In ideal transplanting, the internal organ removed from the donor is immediately transplanted to the recipient, but in many cases, transplanted operations do not immediately happen to occur. It is very important to preserve precious organ for transplantation because the operation is very urgent. There are two kinds of preservation methods for internal organ, in which preservation method at low temperature is intended to reduce metabolism on one hand, while perfusion preservation method is intended to maintain metabolism on the other hand. Many kinds of storage agents are developed in order to apply for these methods and clinically undergone.

Euro-Collin's solution was employed in early stage of transplantation, having validity period of less than 24 hours in liver case and expected to make prolong the validity period. Recently, UW solution was developed by Group of University of Wisconsin (University of Wisconsin, Wahlberg, J. A. et al, Transplantation, 43, pp.5-8, 1987) and applied for storage agent of pancreatic transplantation. This solution is useful for storage agents of not only pancreatic but also liver and kidney transplantation and the validity period of liver has possibly prolonged to 24 hours.

However, even these solutions can not be satisfied still, so new solution is expected to develop and invent in order to preserve viability and effectiveness of internal organs for a long time.

Generally speaking of all kinds of internal organs, functional injury of transplanted organ is inflicted based on a reason why free radicals generated at ischomia or resuming blood flow cause to prompt lipid peroxidation of biological membrane. Therefore, if cell injury caused on generation of lipid peroxidation, can be prevented, it is possible to develop novel effective storage agent.

These problems are greatly related to proliferation and division of the cells. Therefore, it seems to be big possibility of the accomplishing objective if proliferation and division of the cells can be freely controlled. The injury of cells or organs largely relates to active oxygen ($O^-_2$) yielded when hypoxanthin converted from adenosine tri-phosphate (ATP) in cell mitochondria changes to xanthine. Most serious problem come from the injuries, is carcinogenesis phenomenon, in which the cancer formation seems to be composed of two stages of carcinogenesis initiation and promotion. In carcinogenesis initiation stage, several kinds of carcinogenic substances inflict the cell DNA, mutation happens to occur, and normal organs become cancerous by infinite amplification of the cell. The active oxygen affects on the mutation and causes to aging and various plagues by super peroxide generated from the oxygen.

Recently, there are many reports concerning free radical effectiveness on living organ and mechanism of anti-oxidizing agent. As well known anti-oxidizing agents, super oxide dimustarse (SOD) is pointed out as enzyme type, while vitamin E and C, glutathione, carotinoid, flavonoid, saccharide, chelate of iron, uric acid, and albumin are pointed out as non-enzyme type.

There are no reports with respect to proliferation control of cells and preservation of tissue and internal organ. However, it is recently reported that green tea polyphenol shows effects of anti-oxidizing, deodorization action, antibacterial and anti-cancer effect, and is fabricated cheap and large quantities as material of functional foods.

SUMMARY OF THE INVENTION

The present invention relates to a storage agent including polyphenol as an effective ingradient for preservation of an animal cell, tissue and organ. It is preferred that the polyphenol is composed of catechins including epigallocatechin, tannic acid or proanto-dianisidine as a main constituent, the cell is composed of an animal cell including a stem cell, skin cell, mucosa cell, hepatocyte, islet cell, neural cell, cartilage cell, endothelial cell, epidermal cell, osteocyte or muscle cell isolated from human or animal organs, or sperm, ovum or fertilized egg of domestic animals or fishes and the organ includes skin, blood vessel, cornea, kidney, heart, liver, umbilical cord, bowels, nerve, lung, placenta or pancreas.

The storage agent can make protein stabilize by adding the polyphenol to protein type storage agent, play the role of the storage agent by adding the polyphenol to blood, corpuscle or blood platelet, and prevent, treat and improve organ injury caused on an organ transplant operation by adding the polyphenol to organ preserved agent.

Preserved process of animal cell tissue and organ is employed as the storage agent for organ transplant operation.

DETAILED DESCRIPTION OF THE INVENTION

According to the present invention, it is possible to elucidate proliferation mechanism of animal cell, invent and develop novel storage agent for many kinds of internal organs and blood storage, prolong validity period two times longer than the usual, and improve protein stabilizing.

It is concretely possible to preserve normal and useful cells in long term without freezing and freely control the cell proliferation and division by controlling free radicals, which largely relates to the cell proliferation and division.

The present invention provides novel storage agent for internal organ or tissue transplantation, utilizing in a field of cell or tissue engineering and containing polyphenol as an effective component. In addition, we propose preserved process of animal cell or organ by employing as the storage agent for organ transplant operation.

The polyphenol of the present invention consists essentially of catechins, as green tea polyphenols, including epigallocatechin of 3,3,4,5,7-flavopantanol.

Particularly, catechins composed of epigallocatechin as main component are more preferable.

The polyphenol as an effective component of the present invention is abundantly contained in habitual drinks such as tea, green tea, and wine. For example, green tea polyphenol is soluble and purified in water and organic solvents such as ethanol or ethylacetate, and composed of catechins having epigallocatechin (EGCg) as main component.

We can point out anti-oxidizing agents in other compounds having similar effects to the polyphenol, in which super oxide dimustarse (SOD) is pointed out as enzyme type, while vitamin E and C, glutathione, carotinoid, flavonoid, saccharine, chelate of iron, uric acid, and albumin are pointed out as non-enzyme type.

The preferable method in the present invention includes to add a preservative composed of the polyphenols as an effective ingredient to several kinds of known cultured or storage agents for transplanted organs. The above known agents include Euro-Collins solution(Squifflet J. P. et al., Transplant Proc., 13, 693, 1981) or UW solution.

Polyphenol purity of the present invention is possibly employed by ordinary products having more than 60 wt. % purity, further preferably purified one having more than 80 wt. % purity for the cultured or storage agents, though products having more than 60 wt. % purity is easily gotten in the market. Therefore, the more purified, the more effective. However the effective components contained as the storage agents of the present invention, are regardless of the polyphenol purity.

The polyphenols of possibly 0.1 to 50, or preferably 1 to 30 wt. % are added to the above known cultured or storage agents for transplanted organs, when the storage agent described in the present invention is applied for preservation of the animal cells and organs.

And, the polyphenols of possibly 0.1 to 50, or preferably 1 to 30 wt. % are further added to the above Euro-Collin's solution or UW solution which are already clinically employed for transplanted organs, when the storage agent described in the present invention is applied as preservation of the transplantable tissues.

For other example, the polyphenols of 0.1 to 50 wt. % are further previously or later added to a solution of glucose or phosphate on the market, or a solution of poly-oxyethylene or non-ionic surfactant which is added as a storage agent, when the storage agent described in the present invention is applied as preservation of the blood, corpuscle or blood platelet.

Further, the polyphenols of 0.1 to 50 wt. % are further added to a storage solution, which is previously added a fatty acid ester on the market, or possibly added the solution instead of the fatty acid ester, when the storage agent described in the present invention is applied for stabilizing protein.

In addition, the polyphenol of 0.1 to 50 wt. % is possibly added to a storage solution on the market in order to prevent, treat and improve organ injury caused on an organ transplant operation as organ-preserved agent after transplanting an internal organ. A dosage method of the storage agent includes ordinary methods such as an intravenous injection, oral, nasal cavity, suppositor or endermism, and its volume has no limitation depending on symptom or patient age. And the known anti-oxidizing agents of super oxide dimustarse (SOD), vitamin E and C, and glutathione, are possibly further added to the above invented cultured or storage agents for transplanted organs.

The storage agent of the present invention is preferably applied in a temperature of 0 to 37° C., which is relative higher temperature and no necessity of freezing in comparison to the ordinary agents on the market, having relative longer storage period and being superior in the transplanted operation of internal organs.

The cell as defined in the present invention, composes of an animal cell including a stem cell, skin cell, mucosal cell, hepatocyte, pancreatic cell, neurocyte, chondrocyte, endothelial cell, epidermal cell, osteocyte or muscle cell isolated from human or animal organism, or sperm, ovum or fertilized egg of domestic animals or fishes.

The organ as defined in the present invention includes skin, blood vessel, cornea, kidney, heart, liver, umbilical cord, bowels, nerve, lung, placenta or pancreas and so on.

As the result of being interested in the polyphenol, especially its anticancer effect from several years ago and being investigated in the properties, the present inventor found that the polyphenol has unique properties, being easily soluble both in water and organic solvents, this is amphipathic property having hydrophilic and lipophilic natures, being adsorptive activity in protein and extremely low cytotoxity, having anti-oxidized effects of ten times higher than SOD, and freely controlling the animal cell proliferation which is unknown until now.

Many investigators have already reported since 1980s that the polyphenol shows several effects of physiological activities including anti-oxidizing, anti-bacterial, anti-virus and anticancer effect, and controlling cancer proliferation. However there is no report concerning effects on the animal cell proliferation.

Especially, a report with name of <<J. Jankun, S. H. Selman, and R. Swiercz, "Why drinking green tea could prevent cancer", Nature, 387, 5 June, 561, 1997 <<Y. Cao and R. Cao, "Angiogenesis inhibited by drinking tea, Nature, 398, 1 April, 381, 1999>> was recently published on "Nature" and paid world-widely attention.

Green tea polyphenol is recently taken as a functional food because of having effects on anti-oxidizing, deodorizing, anti-bacterial, anticancer and dieting, and other effects of physiological activities (Chemistry and Application of Green tea, Ed. T. Yamamoto et al. CRC Press, Boca Raton New York, 1997). However, it is unknown for the polyphenol to have the preserved effects of the animal cells, tissues and organs.

It seems in past that most researchers had been only interested in the anticancer activity of the polyphenol as an antioxidizing. Therefore, no inventors but the inventor of the present invention were interested in a reason why mammal cells can hibernate in their body temperatures, and methods of freely controlling a proliferation of the normal animal cells. Furthermore, it is naturally impossible for the inventors to discover a reason of recovering their cell properties by normally re-starting cell proliferation and division after hibernation.

As the result of freely controlling animal cell proliferation, this invention opens the way for served as a major breakthrough leading to not only the basic study of cell engineering but also the long time preservation of the cells, tissues and organs.

This invention contributes the progress in frontier medical sciences to find the substance possible to freely control the cell proliferation of basic units composed of living body such as pancreas, liver and kidney, add the substance to ordinary storage agents and give the technology applied for the preservation of both organs and bloods.

According to the present invention, it is possible to preserve the hepatic and pancreatic cells, and the fertilized egg in long period without freezing, by adding the polyphenol to the above known cultured agents, and therefore utilize in a field of the cell and tissue engineering which relate to fabrication of useful substances such as cytokine produced by animal cells. It is possible to preserve in long period without freezing, the transplanted tissues or organs including skin, blood vessel, cornea, kidney, heart, liver, umbilical cord, bowels, nerve, lung, placenta, pancreas, blood, corpuscle or blood platelet, by adding the polyphenol to the above known storage solutions for transplanted tissues or organs.

The storage agent can stabilize protein such as an enzyme, an immunity, an antigen, an immunologically active substance or a physiologically active peptide in solution or dry stages, apply for foods, clinical and medical devices, by adding, mixing or blending the polyphenol to protein type storage agent. Moreover, by adding the polyphenol to organ persevered agent, the novel storage agent plays the role of preventing, treating and improving organ injury that is caused on the transplanting operation.

In conclusion, the present invention can elucidate the proliferated mechanism of the animal cells, and make the validity period prolong at least two times longer than ordinary storage agents in case of preserving blood and organ after transplanting an internal organ by freely controlling animal cell proliferation. Concretely, it is possible to preserve normal and useful cells in long term without freezing and freely control proliferation and division of the cell by controlling free radicals which largely relates to proliferation and division of the cell. In addition, the storage agent of the present invention is possible to be applied in a relative higher temperature and no necessity of freezing in comparison to the ordinary agents on the market, superior in the transplanted operation of internal organs.

EXAMPLE

This invention is further illustrated by the following examples and comparative examples, however is not restricted by the examples.

Example 1 and Comparative Example 1

Rat Fibroblast

L-929 rat fibroblast was cultured in a mixture of Eagle's MEM containing kanamycin of 60 ml/lit and 10% fetal bovine serum(FBS, M. A. Bioproduct, Maryland, USA). New mixture (example 1) which was added the polyphenol of 5 mg/ml to the above mixture, was estimated cell proliferation on the test condition of cell density of $1.76 \times 10^5$ cells/ml in comparison to the mixture of serum medium (comparative example 1). The fibroblast cultured in the mixture of serum medium was started to rapidly proliferate at second day and increased until $2.5 \times 10^6$ cell at fifth day while the fibroblast cultured in the new mixture was not observed to proliferate even at seventh day. However, the fibroblast cultured in the new mixture re-started to proliferate by changing media to the mixture of serum medium (comparative example 1) and increased until $4.5 \times 10^6$ cell at seventh day. It was observed that the fibroblast was possible to sleep in a period of three months.

Example 2 and Comparative Example 2

Porcine Hepatocyte

Porcine hepatocytes were harvested from a pig of approximately 20 kg body weight and cultured in the cultured blood of $2.1 \times 10^5$ cells coated by type 1 collagen, and cultured in Dulbecco's modified Eagle's medium( comparative example 2; DMEM) composed of bovine serum of 100 mg/lit, Penicillin of 50000 unit/lit, Streptomycin of 100 mg/lit, EGF of 0.5 mg/ml, and insulin of 0.25 mg/lit, by changing to the new Eagle's medium a time every three days. Proliferated property of hepatocyte was compared an original Eagle's medium with an improved medium (example 2) which was added the polyphenol of 5 mg/ml to the Eagle's medium.

Porcine hepatocytes in the Eagle's medium were gradually proliferated at beginning to fourth day, and thereafter rapidly proliferated until $5.4 \times 10^6$ cells at seventh day while the hepatocytes cultured in the improved mixture was not observed to proliferate even at seventh day. However, the porcine hepatocytes cultured in the improved mixture re-started to proliferate by changing media to the Eagle's medium similar to case of the L-929 rat fibroblast. The property of hepatocytes (example 2) which were slept a week by adding the polyphenol, and woken up, was sure to be similar level to original hepatocyte by examining D-glucose and Lidocaine clearances in order to check the property of hepatocyte.

Example 3 and Comparative Example 3

Rat Pancreatic Langerhans Inslets

About 2000 pieces of Langerhans inslets were isolated from the pancreas in Wister rat (380 g weight) pancreas and about 200 pieces were cultured as a part of them.

RPMI Medium 1640 (LIFE TECHNOLOGIES; lot No. 1019650) was applied as cultured medium, which was composed of Gibco BRL with L-glutamine, and without glucose, and further added by 10% glucose of 100 mg/dl fabricated in Fetal Bovine Serum (lot No. 29110643, CASERA INTERNATIONAL INC. CANADA), and Antibiotic-Antimycotic (lot No. 1013807, LIFE TECHNOLOGIES).

In example 3, the polyphenol was added to the Medium 1640 in order to become 2% concentration while the polyphenol was not added in comparative example 3. The inslets were cultured a week at 37° C. in the both polyphenol added and not added mediums. The inslets of 50 and 100% were destructed at second and fourth days in the medium (comparative example 3) of the no polyphenol, respectively. On the contrary, the pieces of 100% were not destructed but hibernated at seventh day in the medium (example 3) of the polyphenol.

After about 2000 pieces of inslets were made hibernation a week by adding the polyphenol to the Medium 1640, the polyphenol was removed from the Medium 1640 in order to estimate properties of inslets after hibernation. As the result of examining an insulin workability by applying one step enzyme method of immunity and Insulin-EIA tester (GLAZYME; Wako), it is found that properties of the above inalets of rat pancreas showed normal fimetion similar to the inslets immediately after harvesting.

Example 4 and Comparative Example 4

Preservation of Rat Kidney

Kidney was extracted from Wister rat (380 g weight) under an aesthesia and preserved effects were compared. In comparative example 4, the kidney was preserved 48 hours in UW solution at freeze stage after extracting and washing. On the contrary, in example 4, the kidney was preserved 48 hours in the UW solution at 4° C. after extracting and washing in a novel solution which was composed of further adding the polyphenol of 10 mg/ml to the UW solution, thereafter, continuously perfused 90 minutes in perfusion instrument of isolated kidney, and both specimens were compared their perfused volume, uric volume and creatine clearance. It was found that kidney injury was extraordinary reduced in the novel solution of the present invention in comparison to kidney in only UTW solution.

Example 5 and Comparative Example 5

Enzyme Stabilizer

A novel β-D-galactosidase solution was made by adding the polyphenol of 10 mg/ml(example 5) to ordinary one, incubated 4 weeks at 30° C. and measured an absorbance of 420 nm. The absorbance showed more than 90% in the novel solution, while about 10% in an ordinary solution of no polyphenol (comparative example 5).

Example 6 and Comparative Example 6

Preservation of Blood and Corpuscle

Human blood solution of 2ml was added by a novel solution of 500 μl which was previously made by adding the polyphenol of 10 mg/ml to a saline (example 6). A granule number was counted after 48 hours by applying an automatic counter. The number of the human blood almost unchanged and showed almost same level of immediately after collection in the novel solution, while the number reduced about 30% in ordinary saline (comparative example 6).

Example 7 and Comparative Example 7

Preservation of Blood Platelet

Platelet rich plasma (PRP) was gotten from human blood by a centrifugal separator. PRP of 100 ml was added by a novel solution of 10 ml which was previously made by adding the polyphenol of 10 mg/ml to a saline (example 7),and incubated 3 days at 22° C. Cohesive property of the platelet and its shape were reduced and swollen after 3 days in ordinary saline (comparative example 7). However, above reduction and deterioration were not observed, but almost same level of their initial cohesive property and shape were observed in the novel solution.

Example 8

Intravenous Injection

The polyphenol solution was added to rat blood in order to prevent, treat and improve organ injury caused on an organ transplant operation. A physiological salt solution of 2 ml which was added by the polyphenol of 10 ml/ml, was continually injected into a tail vein of Wister-type male rat (350 g weight) a week by a time a day. The rat was normally alive not only a week but also 3 months.

I claim:

1. A method for preserving a human or non-human organ or animal tissue for transplantation, at in vitro and freeze-free state, comprising storing the animal tissue or organ within a liquid containing green-tea polyphenols;
    said green-tea polyphenols consisting essentially of catechins; and
    prolonged preservation being able to be accomplished by hibernation or sleeping of said animal tissue or organ, with no substantial proliferation of the tissues and/or no substantial injury to the organ so as to normally restart cell proliferation and division after the hibernation,
    and wherein the concentration of the green-tea polyphenols in said liquid is in a range of 0.1 wt % to 30 wt %, calculated on the basis of pure polyphenols,
    and wherein said liquid also contains in addition to the green-tea polyphenols, a culture or conventional storing medium for said tissue or organ selected from the group consisting of UW solution, Euro-Collins solution, glucose, phosphate, non-ionic surfactant or antibiotics.

2. The method according to claim 1, the tissue or organ being preserved as long as about a week or more.

3. The method according to claim 1, wherein an organ is washed with said liquid and thereafter cooled to be preserved as long as about 48 hours or more in a conventional storing medium for isolated organs or tissues, which is UW solution or Euro-Collins solution.

4. The method according to claim 1, wherein said concentration of said green-tea polyphenols in said liquid is selected from a concentration of about 0.1 wt %, about 0.2 wt %, and about 0.5 wt %.

5. The method according to claim 1, wherein said concentration of said green-tea polyphenols in said liquid is selected from a concentration of about 1 wt % and about 2 wt %.

6. A method for preserving human or non-human organ or animal tissue for transplantation, at in vitro, comprising
    immersing the animal tissue or organ in a liquid that contains green-tea polyphenols consisting essentially of catechins, by a concentration in a range of 0.1 wt % to 30 wt %, and also contains a culture or conventional storing medium for said tissue or organ selected from the group consisting of UW solution, Euro-Collins solution, glucose, phosphate, non-ionic surfactant or antibiotics;
    preserving the animal tissue or organ in a state of being hibernated or slept by action of the green-tea polyphenols so that no substantial proliferation of the tissues are occurred and no substantial injury is made on the organ; and
    recovering the animal tissue or organ from the state of being hibernated or slept, by removing the green-tea polyphenols from the animal tissue or organ.

7. The method according to claim 6, wherein said concentration of said green-tea polyphenols in said liquid is selected from a concentration of about 1 wt % and about 2 wt %.

8. The method according to claim 6, wherein said concentration of said green-tea polyphenols in said liquid is selected from a concentration of about 0.1 wt %, about 0.2 wt %, and about 0.5 wt. %.

9. A method for preserving human or non-human organ or animal tissue for transplantation, at in vitro, comprising
    immersing the animal tissue or organ in a liquid that contains green-tea polyphenols consisting essentially of catechins, by a concentration in a range of 1 wt % to 30 wt %, and also contains a culture or conventional storing medium for said tissue or organ selected from the group consisting of UW solution, Euro-Collins solution, glucose, phosphate, non-ionic surfactant or antibiotics;
    preserving the animal tissue or organ in a state of being hibernated or slept by action of the green-tea polyphenols so that no substantial proliferation of the tissues are occurred and no substantial injury is made on the organ; and
    recovering the animal tissue or organ from the state of being hibernated or slept, by removing the green-tea polyphenols from the animal tissue or organ.

10. The method according to claim 6, wherein the animal tissue is pancreatic islets; and the liquid contains Medium 1640 or the other culture medium.

11. The method according to claim 6, wherein the animal tissue or organ is of kidney; and the liquid contains UW solution or the other storing medium.

12. The method according to claim 1, wherein the animal tissue is pancreatic islets; and the liquid contains Medium 1640 or the other culture medium.

13. The method according to claim 1, wherein the animal tissue or organ is of kidney; and the liquid contains UW solution or the other storing medium.

* * * * *